United States Patent [19]

Kolhouse et al.

[11] Patent Number: 5,212,096

[45] Date of Patent: May 18, 1993

[54] GAS CHROMATOGRAPHY/MASS SPECTROMETRY DETERMINATION OF ASCORBATE AND OXIDATION PRODUCTS THEREOF

[75] Inventors: J. Fred Kolhouse; John C. Deutsch, both of Denver, Colo.

[73] Assignee: University of Colorado Foundation, Inc., Boulder, Colo.

[21] Appl. No.: 838,356

[22] Filed: Feb. 19, 1992

[51] Int. Cl.$^5$ .............................................. G01N 33/00
[52] U.S. Cl. ....................................... 436/93; 436/18; 436/96; 436/131; 436/161; 436/173; 73/19.02; 73/23.35
[58] Field of Search ........................... 73/19.02, 23.35; 436/18, 96, 161, 131, 173, 93

[56] References Cited

U.S. PATENT DOCUMENTS

| | | | |
|---|---|---|---|
| 3,852,157 | 12/1974 | Rubenstein et al. | 195/63 |
| 3,935,074 | 1/1976 | Rubenstein et al. | 195/103.5 |
| 4,483,921 | 11/1984 | Cole | 435/7 |
| 5,073,629 | 12/1991 | Dubler et al. | 530/405 |

OTHER PUBLICATIONS

Miller et al. (1990) Free Radical Biol. & Med. 8:95–108.
Taquil et al. (1967) J. Am. Chem. Soc. 89:4176–4185.
Rothenberg et al. (1972) New Engl. J. Med. 286:1335–1339.
Marquez et al. (1990) J. Biol. Chem. 265:5666–5670.
Nichol et al. (1950) Proc. Soc. Exp. Med. 74:52–55.
Frei et al. (1989) Proc. Natl. Acad. Sci. USA 86:6377–6381.
Maguire et al. (1989) J. Biol. Chem. 264:21462–21465.
Ramakrishna-Rao et al. (1990) J. Biol. Chem. 265:844–847.
Weitzman and Gordon (1990) Blood 76:655–663.
Stahelin et al. (1987) in Third Conference on Vitamin C, Burns (ed.) 498:124–131.
Washko et al. (1989) Anal. Biochem. 181:276–282.
Buettner (1988) J. Biochem. Biophys. Methods 16:27–40.
Gey et al. (1987) in Third Conference on Vitamin C., Burns (ed.) pp. 110–120.
Honegger et al. (1986) J. Chromatography 381:249–258.
Ng et al. (1985) Biochem. Pharm. 34:2525–2530.
McMahon (1985) Anal Biochem. 147:535–545.
Knaack et al. (1985) Proc. Natl. Acad. Sci. USA 82:575–579.
Washko et al. (1989) J. Biol. Chem. 264:18996–19002.
Smith (1991) Free Radicals in Biology and Medicine 10:217–224.
Pryor and Godber (1991) Free Radicals in Biology and Medicine 10:177–184.
Dhariwal et al. (1990) Anal. Biochem. 189:18–23.

*Primary Examiner*—James C. Housel
*Assistant Examiner*—N. Bhat
*Attorney, Agent, or Firm*—Greenlee and Winner

[57] ABSTRACT

A method for quantifying in vivo ascorbate concentration in body fluids uses gas chromatography/mass spectrometry (GC/MS). Further provided is a method for measuring redox potentials of body fluid by determining the ratio of in vivo concentration of ascorbate to one or more of its metabolites.

19 Claims, 4 Drawing Sheets

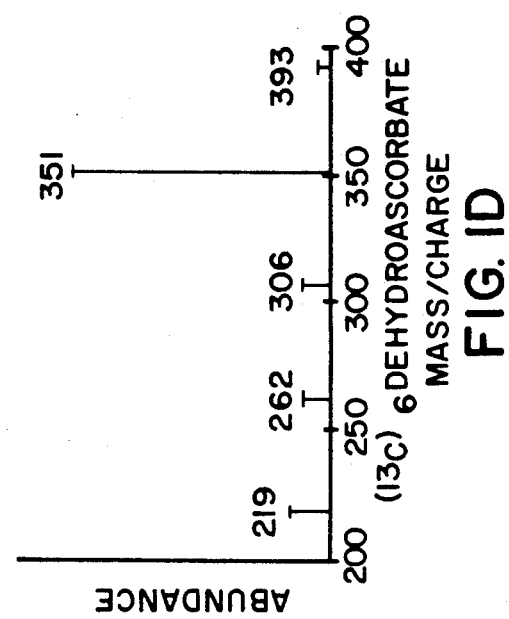
FIG. IC
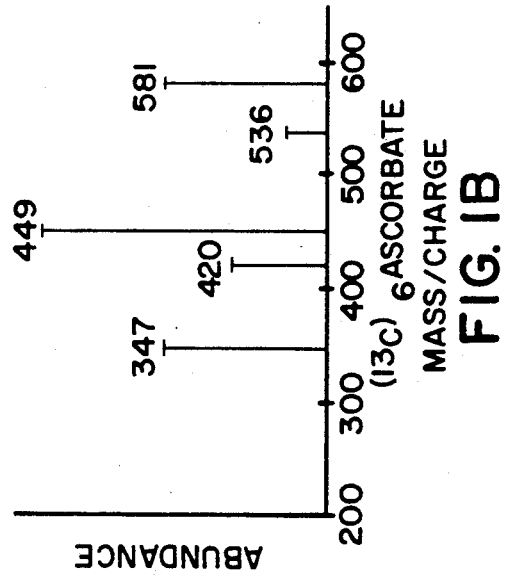
FIG. ID
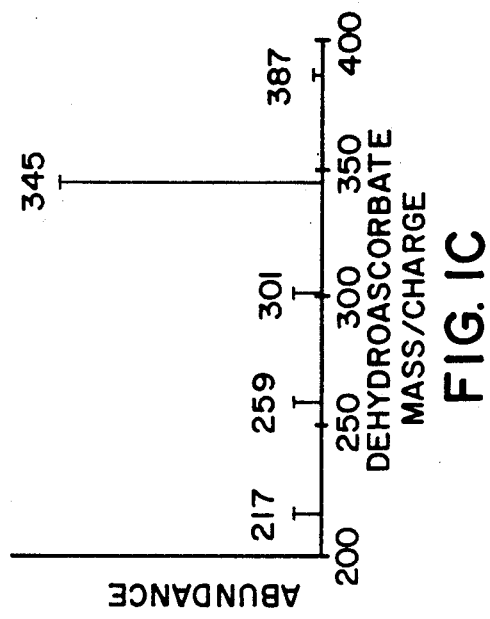
FIG. IA
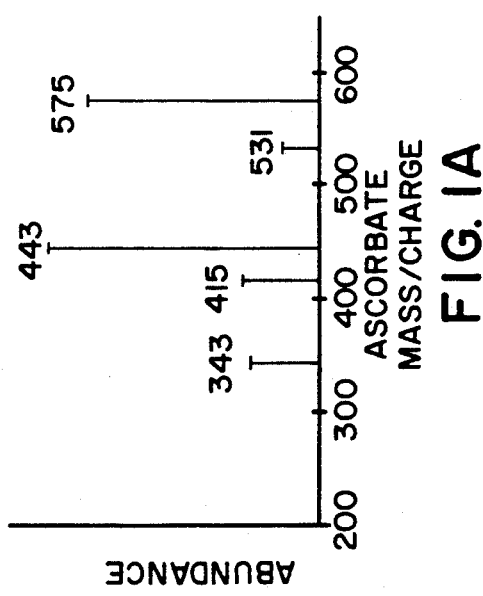
FIG. IB

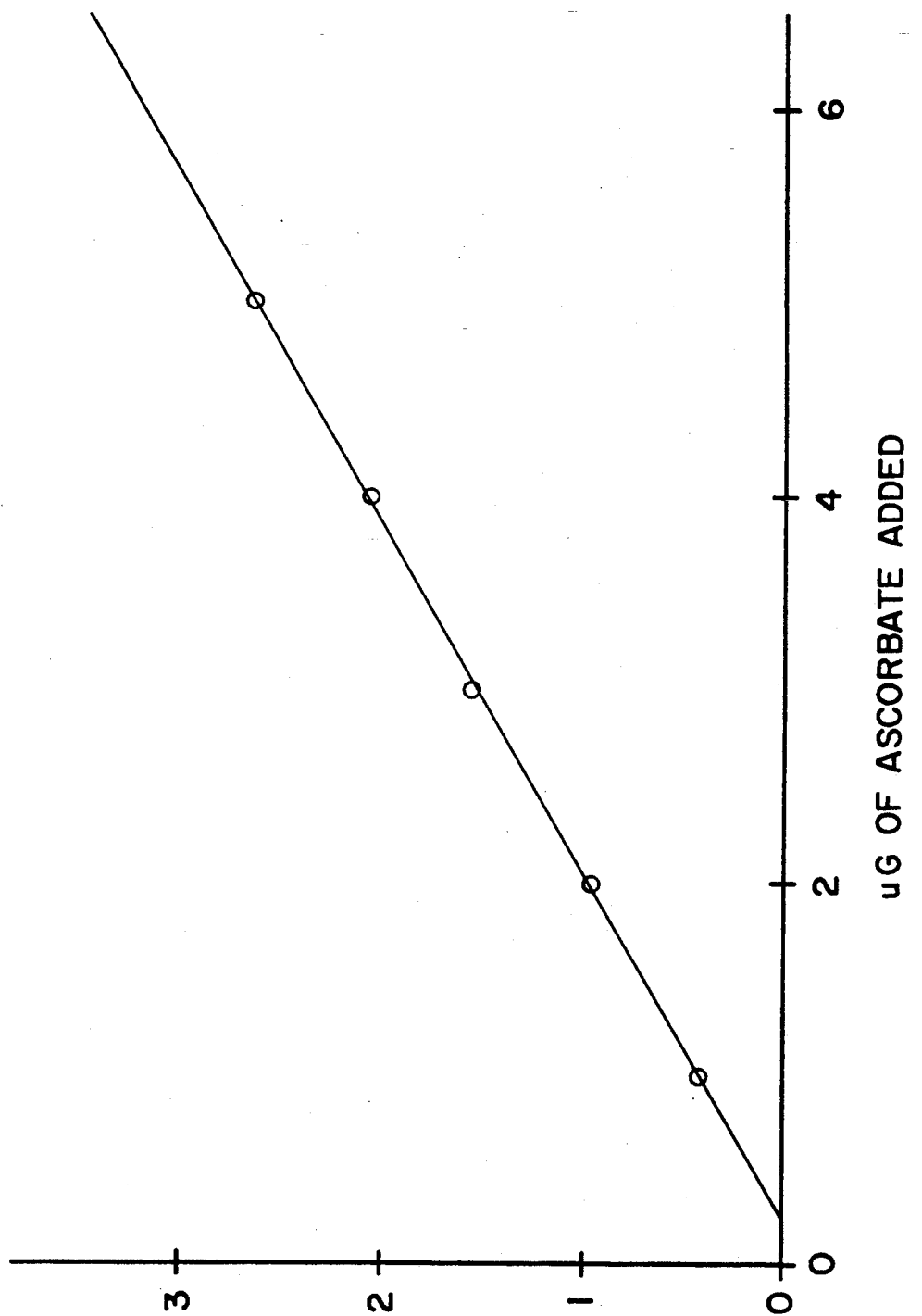

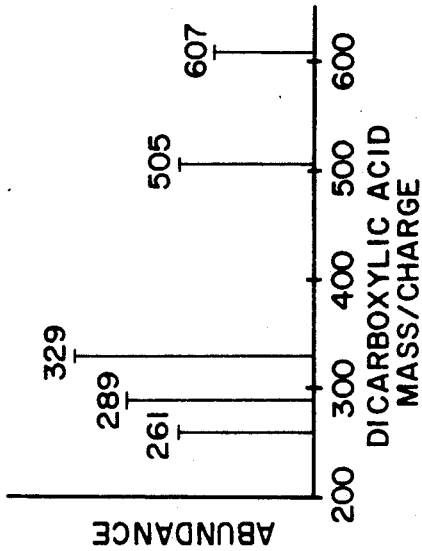
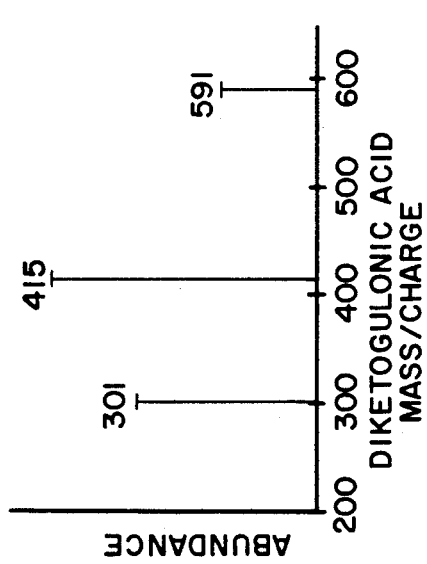
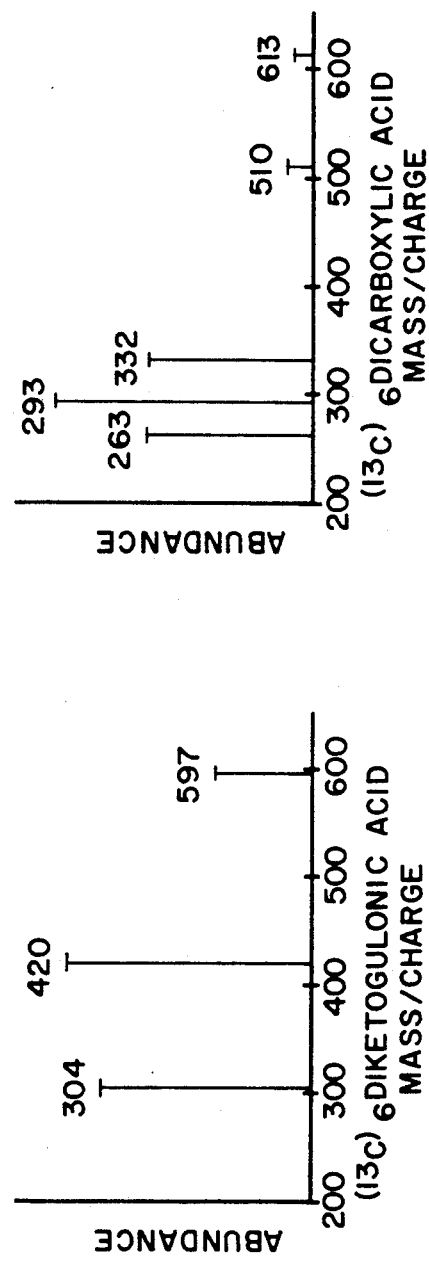

GAS CHROMATOGRAPHY/MASS SPECTROMETRY DETERMINATION OF ASCORBATE AND OXIDATION PRODUCTS THEREOF

The research leading to this invention was partially funded by DHHS Research Grant No. GM26486 The government may have certain rights herein.

BACKGROUND OF THE INVENTION

Ascorbate is a required component in the diet of humans. Ascorbate is the agent which prevents scurvy, and is known to take part in several biological reactions including the formation of collagen, the formation of neurotransmitters, and the degradation of tyrosine (Jaffe G. (1984) in: Handbook of Vitamins (Machlin L. (ed.), Marcel Dekker, Inc. pp. 199-244; Flier J. S. and Underhill L. H. (1986) N. Engl. J. Med. 314:892-902).

Ascorbate is easily oxidized through a free radical intermediate (semi-dehydroascorbate) to form dehydroascorbate, providing electrons to be used in various reactions. Transition metals, particularly Fe(III) and Cu(II) are well described catalysts for oxidizing ascorbate, producing hydrogen peroxide and hydroxyl radicals from molecular oxygen in the process (Miller D. M. et al. (1990) Free Radical Biol. & Med. 8:95-108; Taquil M. M. and Martell A. E. (1967) J. Am. Chem. Soc. 89:4176-4185).

Ascorbate is well-known as an antioxidant in vitro, being used, for example, to prevent the oxidation of reduced folates into oxidized forms in red cell folate assays (Rothenberg S. P. et al. (1972) New Engl J. Med. 286:1335-1339) or as a reducing agent in myeloperoxidase reactions (Marquez L. A. et al. (1990) J. Biol. Chem. 265:5666-70). Furthermore, ascorbate plays an important role as a reducing agent in vivo, as shown by the augmentation caused by ascorbate on the formation of reduced folates from oxidized folates by liver (Nichol C. A. and Welch A. D. (1950) Proc. Soc. Exp. Med. 74:52-55). Recent studies suggest that ascorbate may be the primary extracellular antioxidant in plasma (Frei B. et al. (1989) PNAS (USA) 86:6377-6381) and that other physiologic reducing compounds such as vitamin E, are maintained in the reduced state at the expense of ascorbate (Maguire J. J. et al. (1989) J. Biol. Chem 264:21462-5). Ascorbate has been found to be more effective than glutathione at detoxifying the acetaminophen phenoxyl free radical (Ramakrishna-Rao D. N. et al. (1990) J. Biol. Chem. 265:844-7). Endogenously generated oxidants are thought to be important in carcinogenesis (Weitzman S. A. and Gordon L. I. (1990) Blood 76:655-663), giving ascorbate a potential physiologic role in cancer prevention (Stahelin H. B. et al. (1987) in: Third Conference on Vitamin C (Burns J. et al. (eds) 498, pp. 124-131).

Assays for ascorbate are important to better determine biochemical and physical roles for ascorbate in health and disease. However, the results of currently existing assays must be interpreted with caution since ascorbate is unstable in solution, with measurable degradation in aqueous systems occurring within minutes to hours (Washko P. W. et al (1989) Anal. Biochem. 181:276-82), presumably due to molecular oxygen and traces of contaminating catalytic metals (Buettner G. R. (1988) J. Biochem. Biophys. Methods 16:27-40). Aqueous ascorbate instability is illustrated in the Examples and Table 1 herein. The inventors hereof have found that such degradation also occurs in body fluids. Because body fluids can be stored for days or perhaps weeks prior to ascorbate assay, the measured ascorbate can bear little relation to the in vivo ascorbate concentration As also illustrated in the Examples, freezing may slow the ascorbate degradation process in serum or plasma, but does not arrest it. The extent of ascorbate degradation in collected body fluid is related to the nature of the fluid and the methods of collection and storage. Degradation can vary significantly from one body fluid sample to another.

Inaccurate in vivo ascorbate assays have practical significance, for example, in epidemiologic studies which attempt to correlate plasma ascorbate levels with common fatal human diseases such as cancer (Stahelin H. B. et al (1987) in: Third Conference on Vitamin C (Burns J. et al. (eds) 498, New York Academy of Sciences, pp. 124-131) and ischemic heart disease (Gey K. F. et al. (1987), Id. at pp. 110-120). If changes in ascorbate are occurring in vitro with plasma storage, the epidemiologic data would be subject to error.

Recently, ascorbate assay methods involving HPLC (which provides specificity) and ultraviolet absorption or changes in electrical current or potential (for quantitation) have been described. See Frei B. et al. (1989) PNAS (USA) 86:6377-6381; Washko P. et al. (1989) J. Biol. Chem. 264:13996-19002; Washko P. W. et al. (1989) Anal. Biochem. 181:276-82; and Honegger C. G. et al. (1986) J. Chromatography 381:249-258). However, none of these methods use an internal standard to quantitate the loss of ascorbate in vitro during sample processing and preparation. Other methods, including electron impact mass spectroscopy (Ng Y-C et al (1985) Biochem. Pharm. 34:2525-2530), laser desorption mass spectroscopy (McMahon J. M (1985) Anal. Biochem 147:535-545), and gas chromatography/mass spectroscopy (Knaack D. and Podleski T. (1985) PNAS (USA) 82:575-579) have been used to definitively identify ascorbate, but have not been use to quantitate ascorbate.

Therefore, a need exists for an ascorbate assay that accurately determines loss of ascorbate in vitro during sample storage or processing so that in vivo ascorbate can be calculated.

It would be particularly advantageous if said method for accurately determining in vivo ascorbate concentration could also be used to quantitate the redox potential of body fluids. Quantitation of the redox potential of blood or other body fluids can be a useful means of measuring the oxidative stress of an individual. Oxidative stress can develop, for example, in individuals undergoing oxygen treatment, such as premature infants or persons that have recently undergone surgery. The resulting oxygen toxicity (e.g., adult respiratory distress syndrome (ARDS)) is characterized by the depletion of ascorbate and other reducing agents in the blood or other body fluids. Since the diet is the only source of ascorbate for humans, adequate supplementation to assure normal ascorbate blood levels would be necessary to prevent these complications.

The redox potential of human blood is determined by several processes including the following redox reactions: ascorbate to dehydroascorbate and other metabolites; homocysteine/cysteine to oxidized disulfides; reduced glutathione to oxidized glutathione; Vitamin E to oxidized Vitamin E; and Vitamin A to oxidized Vitamin A. The most sensitive of these indicators of the redox potential may be ascorbate since ascorbate, relative to the other redox species, is the most readily oxidized on exposure to air. Ascorbate's antioxidant function has been found to protect lipids, α-tocopherol, urate and bilirubin from peroxidation by aqueous peroxyl radicals. See Frei B. et al. (1989) PNAS (USA) 86:6377-6381.

Although oxidant stress status is an important indicator of potential disease, (see, e.g., Smith (1991) Free Radicals in Biology and Medicine 10:217-224; and Pryor and Godber (1991), Free Radicals in Biology and Medicine 10:171-184), no method is presently known to the Applicants for measuring the redox potential of body fluids using ascorbate and its oxidation products. Washko P. et al. (1989) J. Biol. Chem. 264:18996-19002, describe the direct measurement of ascorbate and the indirect determination of dehydroascorbate in human neutrophils using high performance liquid chromatography and coulometric electrochemical detection. Dhariwal et al. (1990) Anal. Biochem 189:18-23 measure DHA indirectly by assaying for ascorbic acid, reducing DHA to ascorbic acid, then measuring total ascorbic acid. These methods are not, however, used for the measurement of redox potential. Additionally, Washko and Dhariwal do not use an internal standard, and thus do not account for loss of ascorbate or its metabolites during sample storage. Further, these workers do not measure dehydroascorbate directly and do not measure other ascorbate metabolites at all, and their method is therefore believed to not be an accurate method of measuring in vivo ascorbate concentration, in vivo concentrations of ascorbate metabolites, or redox potential.

Thus, a method for the accurate determination of the in vivo concentration of ascorbate and its metabolites would not only provide an accurate ascorbate assay for epidemological and other studies, but also a sensitive method of measuring an individual's body fluid redox potential. Such method would be useful in epidemiologic studies linking oxidative stress, oxidative injury and disease to in vivo ascorbate metabolism.

SUMMARY OF THE INVENTION

The subject method comprises a GC/MS method for the determination of the in vivo concentration in body fluid of ascorbate and its metabolites. The method is approximately twenty times more sensitive than currently known methods. The subject GC/MS method for the determination of the in vivo concentration of ascorbate comprises quantitating the endogenous ascorbate concentration in body fluid collected in vitro, and calculating the in vivo ascorbate concentration by correcting the quantitated endogenous ascorbate concentration for loss of endogenous ascorbate in vitro prior to GC/MS analysis. The loss of endogenous ascorbate prior to quantitation can be determined by employing an internal standard for ascorbate. In one embodiment, in vivo ascorbate concentration is determined by adding a known amount of ascorbate internal standard to a body fluid (which contains endogenous ascorbate) collected in vitro; partially purifying the endogenous ascorbate and internal standard from other components in the collected body fluid; quantitating endogenous ascorbate and internal standard concentrations by GC/MS analysis; and calculating the in vivo ascorbate concentration by correcting the quantitated in vitro endogenous ascorbate concentration for loss in ascorbate internal standard.

Preferably the internal standard is a nonradioactive heavy isotope of the substance to be measured, which is advantageous in that through mass spectroscopy, it provides more accurate measurement than radiolabelled substances and in that it is safe for the environment. The subject GC/MS method is also useful for determining a body fluid's redox potential, expressed as the ratio of in vivo concentrations of ascorbate to one or more of its metabolites. Thus, a body fluid's redox potential is determined by quantitating by GC/MS analysis the endogenous in vitro concentration of ascorbate and selected metabolites; calculating the in vivo concentrations of ascorbate and selected metabolites by correcting quantitated in vitro endogenous concentrations for loss in each target compound prior to quantitation; and determining the redox potential by calculating the ratio of in vivo ascorbate concentration to the in vivo concentration of one or more of the ascorbate metabolites. The in vivo concentrations of ascorbate and selected metabolites can be accomplished by: adding to the collected body fluid a known amount of an internal standard for ascorbate and each target metabolite to be quantitated; partially purifying endogenous ascorbate and target metabolites and their respective internal standards from other components in the body fluid; quantitating the concentrations of endogenous ascorbate and target metabolites and their respective internal standards by GC/MS analysis; and calculating the in vivo concentrations of ascorbate and target metabolites by correcting the quantitated in vitro concentrations of endogenous ascorbate and metabolites for loss in their respective internal standards. The in vivo concentrations of ascorbate and selected metabolites can be used to determine the redox potential of the body fluid. The redox potential can be expressed as the ratio of in vivo concentrations of ascorbate to any one or combination of its metabolites, including without limitation, DHA and diketogulonic acid isomers. The structures of ascorbate, DHA and ascorbate oxidation products are illustrated in the Detailed Description.

In one embodiment, the redox potential is expressed as the ratio of in vivo concentrations of ascorbate to dehydroascorbate (DHA). In this embodiment, internal standards for ascorbate and DHA are added to a body fluid collected in vitro; the endogenous ascorbate and DHA and their respective internal standards are partially purified from other components in the body fluid; the endogenous ascorbate and DHA and their respective internal standards are quantitated by GC/MS; and the in vivo concentrations of ascorbate and DHA are calculated from the quantitated in vitro concentrations as corrected by the loss in their respective internal standards. The in vivo concentrations of ascorbate and DHA are then used to calculate a redox potential for the body fluid.

As will be apparent to those skilled in the art, the subject method can be used to measure ascorbate and redox potential in fluids other than body fluids, for example, in vitamin preparations containing ascorbate. It can also be used to measure ascorbate and redox potential in tissue samples.

In general terms, a GC/MS method for the measurement of ascorbate concentration in a sample at a first time $T_1$ includes the steps of: (a) conducting a GS/MS quantitation of the ascorbate concentration of the sample at a later time $T_2$; and (b) calculating said ascorbate concentration at $T_1$ by correcting said quantitated concentrations of ascorbate for loss of ascorbate during the time period $T_2$ minus $T_1$.

The redox potential of the sample can be similarly calculated by determining the concentration of ascorbate and at least one oxidation product of ascorbate at $T_1$ and calculating the ratio between the ascorbate and the oxidation product at $T_1$.

BRIEF DESCRIPTION OF THE DRAWINGS

FIG. 1 is the ion fragmentation pattern obtained at 6.76 minutes for A) ascorbate, and B) [$^{13}C$]$_6$-ascorbate, and the ion fragmentation pattern obtained at 4.85 min for C) dehydroascorbate and D) [$^{13}C$]$_6$-dehydroascorbate.

FIG. 2 is a graph demonstrating the increase in the ratio of the 575 dalton ion (ascorbate) compared to the 581 dalton ion ([$^{13}C$]$_6$-ascorbate) when increasing amounts of ascorbate are added to fixed amounts of [$^{13}C$]$_6$-ascorbate.

FIG. 3 is the ion fragmentation patterns of compounds formed during the oxidation of ascorbate and [$^{13}C$]$_6$-ascorbate. The compounds eluting at 6.46 and 6.50 min have a mass consistent with diketogulonic acid from A) ascorbate, and B) [$^{13}C$]$_6$-ascorbate. The compound eluting at 6.38 min has a mass consistent with a dicarboxylic metabolite from C) ascorbate and D) [$^{13}C$]$_6$-ascorbate.

DETAILED DESCRIPTION OF THE INVENTION

Figure 4A:
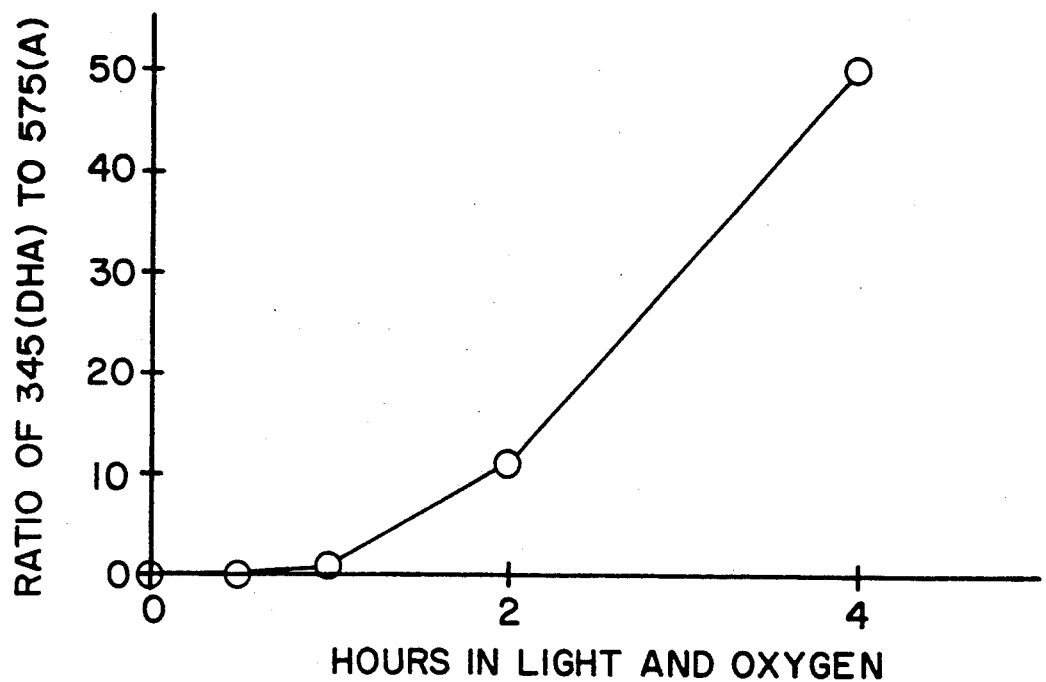
FIG. 4 illustrates the increase in the ions from oxidative metabolites of ascorbate relative to the ascorbate content in A) the 345 dalton ion at 4.85 min (dehydroascorbate, DHA) B) the 415 dalton ions at 6.46 min (open triangle), and 6.50 minutes (closed triangle), and the 505 dalton ion at 6.38 min (open diamond). These are consistent with diketogulonic acid (triangles) and dicarboxylic acid (diamond).

The subject invention provides a method of accurately determining the in vivo concentrations of ascorbate, DHA and other ascorbate metabolites by correcting for the loss of endogenous ascorbate and metabolites during sample storage and preparation. The method is approximately twenty times more sensitive than known methods of ascorbate and DHA measurement. The loss in endogenous ascorbate and metabolites can be determined by using an internal standard for each target compound to be quantitated. By providing a means of accurately determining in vivo concentrations of ascorbate and metabolites, the subject method also provides a reliable and sensitive measurement of the redox potential of a body fluid. As discussed hereinabove, the ratio of in vivo concentrations of ascorbate to DHA and/or other metabolites such as, for example, the diketogulonic acid and ketotrihydroxyadipic acid isomers illustrated herein, is a sensitive indicator of redox potential because ascorbate, relative to other redox species such as homocysteine/cysteine, glutathione and vitamins A and E, is believed to be the first species to be oxidized in vivo.

The subject method has several practical advantages that facilitate quantitation of ascorbate and its metabolites in body fluids. For example, because the subject method employs internal standard that undergoes substantially the same reactions as the target compound, less stringent handling of body fluid samples is permissible compared to prior art methods (Washko P. W. et al. (1989) J. Biol. Chem. 264:18996-19002). Additionally, the subject method has the advantage of abbreviated analysis time due to the combined GC/MS analyses of ascorbate, its selected metabolites and their respective internal standards. Combined GC/MS analyses are possible because ascorbate, DHA and other metabolites identified herein and their respective internal standards have distinct GC column retention times and/or distinct mass spectrometer fractionation patterns. The abbreviated analysis time can result in reduced labor and materials costs. Additionally, the combined GC/MS method can be automated to further reduce process time and labor and materials costs.

As discussed hereinabove, the subject method can be used solely for the determination of in vivo ascorbate concentration or for the determination of in vivo concentrations of both ascorbate and selected metabolites. The structures of ascorbate and one of its metabolites, DHA, are:

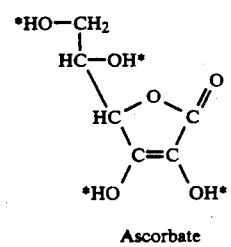

Ascorbate

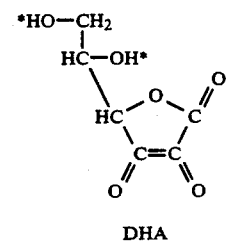

DHA

Derivatizable sites are indicated by an "*". Each derivatization adds a mass of 114 daltons.

Although, all of the metabolites of ascorbate have not been conclusively identified, it is believed that the oxidation products of ascorbate illustrated below are metabolites of ascorbate:

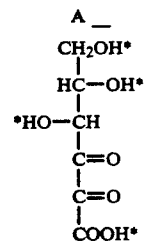

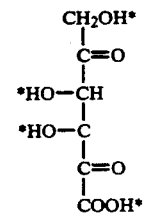

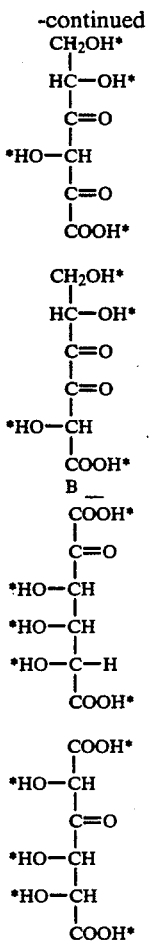

The ascorbate oxidation products of row above are 2,3-diketogulonic acid, 2,5-diketogulonic acid, 2,4-diketogulonic acid, and 3,4-diketogulonic acid, respectively. The row B oxidation products are 1-keto-2,3,4-trihydroxyadipic acid, and 1,3,4-trihydroxy-2-ketoadipic acid, respectively. Chiral centers are marked with a double cross. The identification of these oxidation products is described in Examples 2A and 2B, hereinbelow.

As illustrated in the Examples, the oxidation of ascorbate to DHA can reversed by certain reducing agents such as 2,3-dimercaptopropanol (BAL). In contrast, the oxidation of DHA cannot be reversed by treatment with BAL. The relative irreversibility of the oxidation of DHA indicates that the treatment of body fluid samples with reducing agents like BAL to regenerate ascorbate from its metabolites will not produce an in vitro ascorbate concentration that is substantially the same as the in vivo ascorbate concentration.

After collection of the body fluid, an appropriate internal standard is added, and the sample mixture is prepared for GC/MS analysis. "Body fluid" refers to any body fluid including, without limitation, plasma, serum, cerebral spinal fluid and urine. It can also refer to intracellular fluids such as, for example, the cytoplasmic fraction of leukocytes. It may also apply to fractions and dilutions of body fluids. The source of a body fluid can be a human patient or an experimental animal or other organism. An "internal standard" is a compound added to the sample to be assayed in a known amount and which behaves analogously to the endogenous target compound.

Suitable internal standard compounds for the subject GC/MS method are labeled with a stable isotopic marker. Suitable internal standards for ascorbate and DHA are $[^{13}C]_6$-ascorbate and $[^{13}C]_6$-DHA, respectively. The addition of a known amount of an internal standard allows the determination of the loss (e.g., oxidation, degradation, sample loss) of endogenous compound during storage or sample preparation. As will be appreciated by those skilled in the art, the amount of internal standard to be used is preferably in the same general range as the expected amount of ascorbate or other product being measured.

An "endogenous" compound refers to the compound which is present naturally in the body fluid, i.e., is not exogenously added. When a sample is collected from a patient for assay of a target endogenous compound, the concentration of that compound in the sample at the time of collection is substantially the same as the in vivo level of that target compound in the patient's body fluid. The amount of an endogenous compound in a sample, like ascorbate or DHA, can decrease during the course of body fluid collection, sample storage and/or processing. The in vivo amount or concentration of a compound is its true amount or concentration in the body fluid prior to removal of the fluid from the individual.

The methods of the subject invention are designed to improve the accuracy of determining the in vivo amount or concentration of ascorbate, DHA and other metabolites. However, no representation is made that the methods described herein produce true in vivo concentrations. Rather, it is claimed that, relative to prior art methods, the subject method produces quantitative results that more closely approach the true in vivo amount of the target compound.

An internal standard can be added for each compound to be quantitated. In some instances, where both a first internal standard corresponding to a first target compound and a second internal standard corresponding to a second target compound, are added to the body fluid sample, it is possible that a metabolite of the first internal standard will be identical to the second internal standard. For example, where $[^{13}C]_6$-ascorbate and $[^{13}C]_6$-DHA are used as internal standards for ascorbate and DHA, respectively, the oxidation product of $[^{13}C]_6$-ascorbate is identical to the exogenously added $[^{13}C]_6$-DHA. This does not create a problem in calculating the in vivo DHA concentration because the loss in exogenously added $[^{13}C]_6$-DHA can be calculated from the known amount of $[^{13}C]_6$-DHA initially added to the body fluid, the measured $[^{13}C]_6$-DHA and the measured loss of $[^{13}C]_6$-ascorbate. Alternately, the first and second internal standards can be added to halved portions of the body fluid shortly after collection, followed by separate storage, preparation and GC/MS analyses.

Further, internal standards having different isotope labels can be used so that metabolites of a first internal standard are not identical to a second internal standard. For example, the ascorbate internal standard could utilize a $^{13}C$ isotope while the DHA internal standard utilizes a $D_2$ isotope. Variable dosing of the same isotope label can be employed to avoid identity of a first internal standard metabolite with a second internal standard. Other means of labelling the standards and distinguishing a first internal standard metabolite from a second internal standard are known to those of skill in the art, and such compounds are readily available or can be synthesized from known starting materials by known methods.

To more accurately determine in vivo ascorbate and/or metabolite concentrations, it is important to add the corresponding internal standard shortly after body fluid collection. The internal standard is typically added to the in vitro body fluid within 2-5 hours of collection, preferably within 15-30 minutes, and most preferably within 5 minutes. Where it is desired to measure the plasma in vivo concentrations of target compounds, the internal standard can be added to the plasma after it is separated from the whole blood; i.e., the blood is first collected into a heparinized tube, cooled, then centrifuged at low speed, and a volume of plasma is removed. It is preferred that these steps be completed While the sample is cooled and within 2-3 hours of collection to limit the amount of oxidation prior to addition of the internal standard. However, the following method is more preferred: the blood is collected in a tube containing both heparin and the internal standard; the sample is immediately centrifuged to remove cells; the plasma is then collected. In either embodiment, other ascorbate stabilizing agents can be substituted for heparin.

An "ascorbate-stabilizer" is any composition that can inhibit the degradation of ascorbate in body fluids without significantly interfering with the analysis method. Without wishing to be bound by theory, such inhibition can be accomplished by sequestering of ascorbate from oxidizing agents and/or oxidation catalysts such as transition metals, copper and iron. Ascorbate-stabilizing agents include, without limitation, heparin and some chelating agents such as diethylenepentaacetic acid (DTPA) and deferoxamine. As illustrated in the Examples, heparin and DTPA have been found to be much more effective at stabilizing aqueous ascorbate at $-20°$ C. than EDTA, whose presence actually appears to enhance ascorbate degradation.

The amount of internal standard to be added to the in vitro body fluid varies as a function of the normal concentration range of the in vivo target compound in that body fluid. In plasma, the normal concentration range for in vivo ascorbate has been determined (as described hereinbelow) as between about 7 and 12 $\mu g/ml$. The internal standard is preferably added in an amount to produce a concentration in the in vitro plasma that is within the normal in vivo concentration range. In the case of plasma, the desired internal standard concentration is about 10 $\mu g/ml$. The normal concentration range of the in vivo target compound will vary from one body fluid to another.

Once the internal standard has been added to the body fluid, it is preferred that the sample remain frozen until such time it is prepared (e.g., purification, derivatization) for GC/MS analysis. It was discovered that ascorbate is unstable to a surprising degree at $-20°$. It is therefore preferred that the sample be stored at less than about $-20°$ C., and more preferably at about $-70°$ C.

Preparation of the (thawed) body fluid sample containing internal standards for GC/MS analysis can involve at least partial purification of the target compounds and their corresponding internal standards from other components in the body fluid. It has been found that ascorbate and $[^{13}C]_6$-ascorbate can be partially purified from other plasma or serum components by the following method: combining the plasma or serum with trichloroacetic acid to precipitate components such as nucleic acids and proteins; centrifuging the mixture and decanting the supernatant; washing the supernatant with hydrated ether; and collecting the aqueous phase containing the ascorbate and $[^{13}C]_6$-ascorbate. Other methods for partially purifying ascorbate and/or its metabolites from serum or for partially purifying ascorbate and/or its metabolites from other body fluids are known to those of skill in the art.

By "derivatization" is meant the chemical conversion of the target and internal standard compounds to analogs having improved solubility, different mass to charge ratio, increased volatility, etc., to facilitate separation and identification on a GC/MS. A preferred procedure involves converting the target and internal standard compounds to their silyl derivatives. Means and methods of silating compounds for this purpose are known in the art, see, e.g., Knapp D. R. (1979) Handbook of Analytical Derivatization Reactions (John Wiley & Sons, New York); Bierman C. J. et al. (1986) J. Chrom. 357:330-334.

As discussed hereinabove, it is preferred that the subject GC/MS analyses be conducted simultaneously. However, the individual GC/MS analyses can be conducted separately. Separate analyses may be desirable where, for example a metabolite of a first internal standard is identical to a second internal standard.

EXAMPLES

Example 1

GC/MS Measurement of Ascorbate and DHA

Example 1A

Mass Spectra of Ascorbate and DHA and their $[^{13}C]_6$-Internal Standards

The mass spectra of ascorbate and DHA and their respective $[^{13}C]_6$-internal standards were determined as described herein. $[^{13}C]_6$-ascorbate (96.1 atom percent $[^{13}C]$) was purchased from MDS Isotopes, Montreal, Canada. The derivatizing agent, N-methyl N-tertbutyl-dimethyl-silyltrifluoroacetamide (MTBDMS) was purchased from Pierce, Rockford, Ill. L-ascorbate oxidase was purchased from Sigma Chemicals, St. Louis, Mo.

Ascorbate oxidase was used to make DHA from ascorbate, and make $[^{13}C]_6$-dehydroascorbate from $[^{13}C]_6$-ascorbate. DHA and $[^{13}C]_6$-dehydroascorbate were made by adding 1-6 $\mu g$ ascorbate or $[^{13}C]_6$-ascorbate to 100 units of dry buffered (pH 5.6) ascorbate oxidase suspended in 600 $\mu l$ of water. The reaction was carried out at 22° C. for 30 min. Each reaction mix was then derivatized. Derivatization of the ascorbates and DHAs were prepared by drying 1-10 $\mu g$ of ascorbate in a Savant drying centrifuge and adding 10 $\mu l$ of MTBDMS and 100 $\mu l$ acetonitrile to the dry ascorbates Stabler S. P. et al. (1987) Anal. Biochem. 162:185-196; Marcell P. D et al. (1985) Anal. Biochem. 150:58-66). The mixtures were allowed to react at 40° C. for 1-2 hrs and at room temperature for up to 24 additional hrs. Based on GC/MS, the majority of the derivatization appeared to occur in the first 60 min.

Gas chromatography was carried out on a Hewlett-Packard 5890A gas chromatograph running a temperature gradient of 30° C. per min from 80° C. to 300° C. on a 10 meter SPB-1 Supelco Capillary Column from Belfont, Pa. Mass spectroscopy was carried out on a Hewlett-Packard 5971A Mass Detector with the electron multiplier at 2400 volts. One to 4 $\mu l$ samples were applied to the column.

Based on the structure of ascorbate the derivatized species was predicted to have a mass of 632 daltons and the [$^{13}$C]$_6$-ascorbate a mass of 638 daltons. Since a common ion of MTBDMS derivatized compounds involves removal of a 57 dalton t-butyl group (Stabler S. P. et al. (1987) Anal. Biochem. 162:185–196; Marcell P. D et al. (1985) Anal. Biochem. 150:58–66), ion scanning was performed for ascorbate at a mass of 575 daltons. The 575 dalton ion was detected at a retention time of 6.76 minutes. The fragmentation pattern at this retention time showed ion peaks of 575, 531, 443, 415 and 343 daltons (FIG. 1A). When [$^{13}$C]$_6$-ascorbate was run in the same manner, but monitored at 581 daltons, a major ion peak also occurred at 6.76 minutes. The fragmentation pattern for this species gave ions of 581, 536, 449, 420 and 347 daltons (FIG. 1B).

Based on the structure of DHA, the derivatized mass was predicted to be 402 daltons with the M-57 fragment at 345 daltons. The 345 dalton ion occurred at 4.85 minutes. The fragmentation pattern showed ions at 387, 345, 301, 259 and 217 daltons (FIG. 1C).

The M-57 peak for [$^{13}$C]$_6$-dehydroascorbate was expected at 351 daltons. When scanned at 351 daltons, a major peak occurred at 4.85 minutes, with ions at 393, 351, 306, 262 and 219 daltons (FIG. 1D). The ascorbate oxidase reaction did not completely oxidize [$^{13}$C]$_6$ ascorbate or ascorbate to [$^{13}$C]$_6$-dehydroascorbate or DHA under the conditions described above since based on GC/MS, up to 50% of the unreacted substrate remained (not shown). By 18 hrs the reaction has essentially removed all ascorbate.

Example 1B

Quantitation of Ascorbate and DHA by GC/MS

To test the ability of GC/MS to quantitate ascorbate in an ascorbate concentration range similar to that found in plasma, GC/MS quantitation was conducted for aqueous solutions containing increasing amounts of ascorbate added to a standard amount (2 μg) of [$^{13}$C]$_6$-ascorbate. The ratio of the 475 dalton to the 581 dalton ion was measured at 6.76 minutes and compared to the amount of ascorbate added. As shown in FIG. 2, there is a linear relationship between the quantity of ascorbate added to the defined quantity of [$^{13}$C]$_6$-ascorbate and the ratio of the 575 to 581 dalton ions. The correlation (r) between the increase in added ascorbate to the increase in the ratio of ions was greater than 0.997.

The lower limit of detection of ascorbate was also determined. As little as 50 femtomoles (9 pg) was detectable with a signal to noise ratio of 3 to 1.

For quantitation of ascorbate and [$^{13}$C]$_6$-ascorbate in aqueous solutions and body fluids, standard curves were constructed by graphing the peak heights of the M-57 peaks as a function of increasing concentration of ascorbate and [$^{13}$C]$_6$-ascorbate, respectively. Likewise, to quantitate the DHA and [$^{13}$C]$_6$-dehydroascorbate, a standard curve can be constructed by methods known to those of skill in the art. Such a curve is found in Dhariwal et al. (1990) Anal. Biochem. 189:18–23.

Example 2

Identification and Quantitation of DHA Oxidation Products

Example 2A

Mass Spectra of DHA Oxidation Products

Aqueous solutions of ascorbate and [$^{13}$C]$_6$-ascorbate (100 μg/ml) were left standing at room temperature. Samples were then taken from these solutions at 24, 48 and 72 hours, derivatized and run on the GC/MS as described hereinabove. Comparisons were then made between ascorbate and [$^{13}$C]$_6$-ascorbate metabolites to identify species with similar retention times and fragmentation patterns that differed by 6 or some other integer mass units, thus ensuring that the compounds identified were metabolites of ascorbate. Three major degradative species other than DHA were identified both in ascorbate and [$^{13}$C]$_6$-ascorbate solutions. Two of the three compounds had identical masses and fragmentation patterns but differed in retention time. These had a predicted derivatized mass of 648 daltons when formed from ascorbate and 654 daltons when formed from [$^{13}$C]$_6$-ascorbate based on measured peaks (M-57) of 591 and 597 daltons (FIGS. 3A and 3B). This data is consistent with these compounds being 2,3-dioxogulonic acid and/or related isomers (Formulas A I–IV above). An additional species was found which had a predicted derivatized mass of 664 and 670 daltons based on measured peaks (M-57) of 607 and 613 daltons (FIGS. 3C and 3D). Although the identification of this compound is not positive, the mass and fragmentation pattern is consistent with a 6 carbon dicarboxylic acid with a molecular formula of $C_6H_8O_8$. Although the $C_6H_8O_8$ dicarboxylic acid species would be predicted to have five derivatizable sites (Formulas B I-II above), the species tentatively identified would have only four of these sites derivatized. It is possible that steric difficulties prevented all five potential sites from being derivatized. Although other structures are possible, it is believed that the structures of Formulas A and B are the most likely oxidation products of DHA.

Example 2B

Figure 4B:
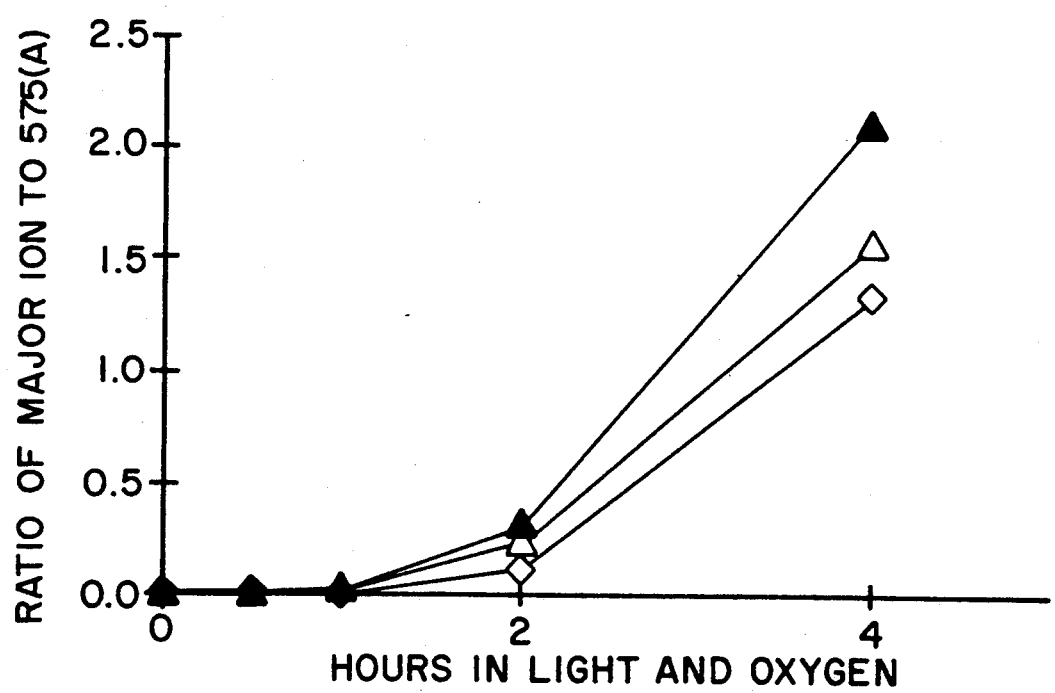

Oxidation of DHA Results in an Increase in Diketogulonic and $C_6$-Dicarboxylic Acid Isomers 100 μM aqueous solutions of ascorbate and [$^{13}$C]$_6$-ascorbate were subjected to four combinations of oxidative conditions: either exposure to direct light from a 50 watt lamp at 10 cm distance or darkness, simultaneously with either argon or oxygen bubbling (2 l/min) though the solutions. 10 μl aliquots were taken from these solutions at the start and at various intervals for 6 hours. These aliquots were dried, derivatized and examined by GC/MS as described herein, monitoring selectively for ascorbate, dehydroascorbate, diketogulonic acids and the $C_6$-dicarboxylic acid species. As shown in FIG. 4A, the relative amount of DHA (345 to 575 ratio) increased by greater than 50-fold over time in the solution exposed to light and oxygen. Following the increase in DHA, there was an increase, as shown in FIG. 4B, in the two species tentatively identified as isomers of diketogulonic acid and the $C_6$-dicarboxylic species.

As shown in Table 1, oxygen appeared to be more potent at inducing ascorbate breakdown than was light, but some ascorbate breakdown occurred even when the solutions were kept in the dark under argon.

TABLE 1

ASCORBATE DEGRADATION IN AQUEOUS SOLUTION[A]
The relative ratios of ascorbate oxidative metabolites to ascorbate (575) after 4 hours in light or dark with either oxygen or argon. The ions represent dehydroascorbate (345), diketogulonic acid (415) and the proposed dicarboxylic acid species (505)

| | | | Exposure Conditions and Exposure Times | | | |
|---|---|---|---|---|---|---|
| Ions | Retention time in min. | Starting material no exposures | Argon + dark 4 hrs. | Argon + light 4 hrs. | Oxygen + dark 4 hrs. | Oxygen + light 4 hrs. |
| 345 | 4.85 | 0.002 | 0.27 | 0.20 | 8.50 | 50.00 |
| 415 | 6.46 | 0 | 0 | 0 | 0.40 | 1.55 |
| 415 | 6.50 | 0 | 0 | 0 | 0.40 | 2.10 |
| 505 | 6.38 | 0 | 0 | 0 | 0.18 | 1.33 |

[A]100 μM ascorbate solutions

Example 2C

DHA Oxidation Products Cannot be Reduced to Ascorbate by BAL

Studies were performed to determine the reversibility of the oxidation of ascorbate using 2,3-dimercaptopropanol (BAL) (Sigma Chemicals) which reduces DHA to ascorbate (Washko P. et al. (1989) J. Biol. Chem. 264:18996-19002). A 100 μg/ml solution of ascorbate was oxidized using oxygen and light. After 5 hours of exposure to a 50 watt light at 10 cm and 2 l/min oxygen the samples were dried, derivatized and examined by GC/MS as described herein. The ascorbate was observed to decrease from 100 μg/ml to 48 μg/ml. After adding 50 mM BAL for 15 minutes, which was more intense reduction than that previously used (10 mM) to totally reduce DHA to ascorbate (Washko, P. et al. (1989)), the ascorbate increased to only 91 μg/ml. A relative increase in the 345 dalton ion at 4.85 minutes (DHA) was present in the oxidized sample, and that ion decreased to values below that in the starting material after 15 minutes of BAL exposure. Therefore, a small but significant quantity approximately 10%) of the initial ascorbate could not be recovered as ascorbate and was oxidized to products that could not be reduced by BAL.

Example 3

Effects of Chelators on Extent of Ascorbate Oxidation in Aqueous Solutions

The effect of chelators on aqueous ascorbate solutions was examined by freezing (−20° C.) a 100 μM solution of ascorbate for 48 hours in the presence of either EDTA, DTPA, FeCl$_3$ or CuCl$_2$ with an excess of EDTA or DTPA, or metal ions without chelators. Four ml aliquots of a 100 μM solution of ascorbate were added to tubes with either 18 μmol K$_3$EDTA, 3 μmol DTPA (diethylenepentaacetic acid, Kodak Chemicals, Rochester, N.Y.) or no chelator, and which additionally had either 1.3 μmol FeCl$_3$, CuCl$_2$ or an equal volume of H$_2$O. These samples were immediately frozen for 48 hours at −20° C. prior to examination by GC/MS. After thawing 1-5 mcg [$^{13}$C]$_6$-ascorbate internal standard was added depending on expected results. As shown in Table 2, ascorbate degradation occurred to a greater extent in EDTA solutions compared to either DTPA solutions or solutions with no chelator or metals added. DTPA was better at protecting ascorbate than EDTA when either copper or iron was added. However, neither DTPA or EDTA was efficient at protecting ascorbate from degradation by FeCl$_3$.

TABLE 2

EFFECT OF CHELATION ON METAL ION DEGRADATION OF ASCORBATE

| Sample | Ratio of Ascorbate To Internal Standard (575/581) | Relative Abundance Of Internal Standard (581)[c] |
|---|---|---|
| Control[a] | 1.00 ± 0.08 | 1.00 ± 0.12 |
| DTPA | 1.00 ± 0.02 | 0.33 ± 0.02 |
| EDTA | 0.82 ± 0.06[b] | <0.01 |
| CuCl$_2$ | 0.44 ± 02[b] | <0.01 |
| DTPA/CuCl$_2$ | 0.62 ± 0.05 | 0.32 ± 0.01 |
| EDTA/CuCl$_2$ | 0.28 ± 0.02 | 0.39 ± 0.10 |
| FeCl$_3$ | 0.73 ± 0.08 | 0.13 ± 0.07 |
| DTPA/FeCl$_3$ | 0.40 ± 0.10 | 0.28 ± 0.04 |
| EDTA/FeCl$_3$ | 0.04 ± 0.01 | 0.25 ± 0.04 |

[a]Control = 100 μM solution of ascorbate frozen at −20° for 48 hrs. The mean of three samples was set at 1.
[b]Estimate based on 443/449 due to low abundance of 575/581.
[c]The internal standard was added after the freeze-thaw and was present only during processing of the samples. The relative loss in internal standard represents both oxidation of the internal standard by the test solution during processing and interference with derivatization by test solutions. This relative abundance is only semi-quantitative since it is based on a single ion response.

Example 4

Measurement of Ascorbate and Metabolites in Plasma

Example 4A

GC/MS Quantitation of Ascorbate in Plasma

The ascorbate content in human plasma was determined by correcting the measured in vitro endogenous ascorbate for loss of ascorbate during sample processing as indicated by loss of internal standard. The blood of three fasting, healthy subjects was drawn into 10 ml syringes and added to vacuum phlebotomy tubes containing K$_3$EDTA or heparin. The cells were separated from the plasma by low speed (3,000×g) centrifugation for 5 min at 4° C. One hundred μl aliquots of plasma were added to known amounts (2 μg) of [$^{13}$C]$_6$-ascorbate. Ten μl aliquots of 100% (w/v) trichloroacetic acid (TCA) (Sigma Chemicals, St. Louis, Mo.) were added to plasma samples while vortexing, followed by 890 μl of H$_2$O. The solutions were centrifuged at 3000×g for 10 minutes and 500 μl of supernatant was removed and washed three times with 1.5 ml hydrated ether. The aqueous phase was dried by vacuum centrifugation and 10 μl of MTBDMS and 100 μl of acetonitrile were added followed by incubation at 40° C. for 2 hours. The solutions were then centrifuged at 30,000×g for 10 minutes and 50 μl of supernatent was removed for analysis. The samples were analyzed by GC/MS as described hereinabove. After accounting for loss of endogenous ascorbate during sample processing as reflected by loss of internal standard, the plasma ascorbate levels were found to range from 7 to 12 μg/ml (40 to 70 μM). The standard deviation in ascorbate concentration of five aliquots of plasma from a single blood draw was less than 10%.

Heparinized plasma was then examined after the addition of known quantities of unlabeled ascorbate. Internal standard was included. A standard curve to assess the effect of adding unlabeled ascorbate to plasma was carried out by allocating fresh heparinized plasma into 3 separate 1 ml aliquots. Each plasma aliquot was diluted with either 50 μl of H$_2$O (final volume 1.05 ml), 50 μl of 40.0 μg/ml ascorbate in H$_2$O or 50 μl of 80.0 μg/ml ascorbate in H$_2$O (net increase of 1.90 μg/ml and 3.80 μg/ml, respectively). These samples were derivatized and analyzed on GC/MS as described herein. All samples were run in triplicate or quadruplicate and the mean and standard deviation were calculated. As shown in Table 3, an excellent quantitative correlation existed between the predicted and measured increments of ascorbate and dehydroascorbate in these plasma samples demonstrating the accuracy of this method in determining the ascorbate content in plasma.

TABLE 3

The Measured Increase in Ascorbate After the Addition of Known Quantities of Ascorbate or Dehydroascorbate to Plasma

|  | Measured Value |
|---|---|
| Ascorbate Added | |
| 0 | 8.0 ± 0.2 µg/ml |
| 1.90 µg/ml | 9.9 ± 0.3 µg/ml |
| 3.80 µg/ml | 11.8 ± 0.2 µg/ml |
| Dehydroascorbate Added | |
| 0 | 1.6 ± 0.1 µg/ml |
| 1.70 µg/ml | 3.2 ± 0.1 µg/ml |
| 3.40 µg/ml | 4.9 ± 0.2 µg/ml |

Next, a human subject had plasma ascorbate levels determined prior to and at intervals after the oral administration of 100 mg/kg of ascorbate. Plasma was collected, processed, derivatized and GC/MS analyzed as described hereinabove. The plasma ascorbate increased 3-fold within 1 hour of the ingestion of ascorbate and remained elevated for the next 3 hours providing evidence of specificity of the GC/MS assay for plasma ascorbate when taken together with the previous results.

Example 4B

Oxidation of Ascorbate in Plasma and Serum Under Storage Conditions

After ascorbate content in fresh plasma was shown to be quantifiable based on the ratio of known amounts of exogenous $[^{13}C]_6$-ascorbate to endogenous ascorbate, studies were carried out to examine the stability of endogenous plasma ascorbate with freezing. The experiments were designed to either add exogenous $[^{13}C]_6$-ascorbate before freezing based on the assumption that breakdown of exogenous $[^{13}C]_6$-ascorbate and endogenous ascorbate would proceed at an identical rate, or to and exogenous $[^{13}C]_6$-ascorbate after freezing the sample for extended periods, allowing the endogenous ascorbate to degrade while the standard was undegraded.

Human plasma was collected in 10 ml syringes and added to vacuum phlebotomy tubes containing $K_3$EDTA, heparin or no anticoagulant. Samples with DTPA were prepared by placing 35 or 70 µl of a 4% (w/v) solution of DTPA into 5 ml borosilicate tubes. Plasma was processed immediately while serum tubes were allowed to coagulate for 4 hours at room temperature prior to freezing.

Plasma and serum samples were stored at −70° C. and −20° C. for 1 to 20 days, either with or without 2 µg $[^{13}C]_6$-ascorbate. Cell free plasma samples were made by passing the plasma through a 0.22µ filter. Metal salts were added to plasma by adding equal volumes of plasma (approximately 7 mM final concentration of $K_3$EDTA, DTPA or heparin) to either 5 or 10 mM solutions of $FeCl_2$, $FeCl_3$, $CuCl_2$, $MgCl_2$, $CaCl_2$ or NaCl, then freezing the solutions at −20° C. for 96 hrs. On thawing, 200 µl of sample solution was precipitated with 20 µl of TCA, brought to a final volume of 1 ml with $H_2O$, and derivatized and GC/MS analyzed as described above.

The ascorbate content of plasma collected in $K_3$EDTA was found to decrease by greater than 80% after 24 hours at −20° C., from 8.99+/−0.34 µg/ml when fresh to 1.66+/−0.16 µg/ml after freezing. When internal standard $[^{13}C]_6$-ascorbate was added to $K_3$EDTA chelated plasma prior to freezing at −20° C., a relative loss of endogenous ascorbate to exogenous internal standard was also noted (9.99+/−0.34 µg/ml when fresh, 6.00+/−0.37 µg/ml after −20° C. freezing). This signified that under these circumstances the endogenous plasma ascorbate was being degraded more rapidly than the exogenous $[^{13}C]_6$-ascorbate which is added to plasma after EDTA chelation of whole blood. This may imply that the endogenous ascorbate is partially sequestered after the addition of EDTA, and that equilibrium was not reached with the exogenous internal standard prior to freezing. Aliquots frozen at −70° C. with $K_3$EDTA and the internal standard did not show *relative* endogenous ascorbate loss (ascorbate value of 8.81+/−0.79 µg/ml after 24 hours). Degradation of ascorbate in $K_3$EDTA occurred, however, based on the ascorbate content measured in aliquots frozen at −70° C. when internal standard was added after thawing (ascorbate value down to 6.90+/−0.15 µg/ml from 8.99+/−0.34 µg/ml). In all instances, as the ascorbate levels decreased in the $K_3$EDTA plasma samples, a corresponding increase was noted in the 345 dalton ion (DHA) eluting at 4.85 minutes.

Heparinized plasma and serum frozen at −20° C. both exhibited approximately 20% degradation of endogenous ascorbate after 24 hours, in contrast to the 80% degradation found in the $K_3$EDTA plasma samples. At −70° C., no significant degradation of ascorbate was found in either heparinized plasma or serum stored up to two weeks.

When DTPA, EDTA and heparin were compared in their ability to protect plasma ascorbate at −20° C., there was no significant difference between heparin or DTPA. Heparinized or DTPA chelated plasma had greater than 7-fold higher level of ascorbate than an identical sample of EDTA chelated plasma.

While various embodiments of the present invention have been described in detail, it is apparent that modifications and adaptations will occur to those skilled in the art. However, it is to be expressly understood that such modifications and adaptations are within the spirit and scope of the present invention, as set forth in the following claims.

We claim:

1. A method for determination of in vivo ascorbate concentration in a body fluid comprising the steps of:
   (a) combining a known amount of ascorbate internal standard with a body fluid collected in vitro, said body fluid comprising endogenous ascorbate;
   (b) at least partially purifying said endogenous and internal standard ascorbate from other components in said in vitro body fluid;
   (c) quantitating said endogenous and internal standard ascorbate concentrations in said purified in vitro body fluid of step (b) by gas chromatography/mass spectrometry analysis; and
   (d) determining the in vivo ascorbate concentration by correcting the quantitated in vitro endogenous ascorbate concentration for endogenous ascorbate loss as reflected by the loss in said known amount of internal standard.

2. The method of claim 1, wherein the ascorbate internal standard is [$^{13}C$]$_6$-ascorbate.

3. The method of claim 1, wherein the ascorbate internal standard is $D_2$-ascorbate.

4. The method of claim 1, wherein the purified endogenous and internal standard ascorbate of step (b) are derivatized prior to gas chromatography/mass spectrometry analysis.

5. The method of claim 1, wherein the body fluid is selected from the group consisting of serum, plasma and leukocyte cytoplasm.

6. The method of claim 1, wherein an ascorbate-stabilizing agent is added to said collected in vitro body fluid before step (b).

7. The method of claim 6, wherein said ascorbate-stabilizing agent is selected from the group consisting of DTPA, deferoxamine and heparin.

8. A method for determining the in vivo body fluid concentrations of ascorbate and metabolites thereof, comprising the steps of:
   (a) combining a known amount of an internal standard for ascorbate and each of said metabolites to be quantitated with body fluid collected in vitro, said body fluid comprising endogenous ascorbate and endogenous ascorbate metabolites;
   (b) at least partially purifying said endogenous ascorbate, endogenous ascorbate metabolites, ascorbate internal standard and metabolite internal standards in said purified body fluid of step (a) from other components in said body fluid;
   (c) quantitating the concentrations of said endogenous ascorbate, endogenous metabolites, ascorbate internal standard and metabolite internal standard by gas chromatography/mass spectrometry analysis; and
   (d) determining the in vivo concentration of ascorbate and metabolites by correcting the quantitated in vitro concentrations of endogenous ascorbate and endogenous metabolites for the endogenous ascorbate and metabolites loss as reflected by the loss of ascorbate and metabolite internal standards, respectively.

9. The method of claim 8, wherein the quantitation process of step (c) is carried out by combined gas chromatography/mass spectrometry.

10. The method of claim 8, wherein said metabolites of ascorbate comprise one or more members selected from the group consisting of DHA, 2,3-diketogulonic acid, 2,5-diketogulonic acid, 2,4-diketogulonic acid, 3,4-diketogulonic acid, 1-keto-2,3,4-trihydroxyadipic acid, and 1,3,4-trihydroxy-2-ketoadipic acid.

11. The method of claim 8 wherein the ascorbate internal standard is selected from the group consisting of [$1^{13}C$]$_6$-ascorbate and $D_2$ ascorbate.

12. The method of claim 8, wherein the DHA internal standard is selected from the group consisting of [$^{13}C$]$_6$-DHA and $D_2$-DHA.

13. The method of claim 8, wherein said internal standards are combined with body fluids within 30 minutes of collection.

14. The method of claim 8, wherein the endogenous and internal standard ascorbate and the endogenous and internal standard DHA are derivatized prior to gas chromatography/mass spectrometry.

15. The method of claim 8, wherein the partial purification process comprises:
   (a) treating the body fluid and internal standard of step (a) with trichloroacetic acid;
   (b) centrifuging the trichloroacetic acid mixture and decanting supernatent; and
   (c) washing said supernatent with hydrated ether; and
   (d) collecting the aqueous phase.

16. The method of claim 8, wherein the body fluid is selected from the group consisting of serum, plasma and leukocyte cytoplasm.

17. The method of claim 8, wherein an ascorbate-stabilizing agent is added to said collected in vitro body fluid after addition of said internal standards but before said partial purification step.

18. A method for measuring the redox potential of a body fluid by determining the ratio between in vivo concentrations of ascorbate and metabolites thereof, comprising calculating the ratio of the in vivo concentration of ascorbate to the in vivo concentrations of at least one member selected from the group consisting of DHA, 2,3-diketogulonic acid, 2,5-diketogulonic acid, 2,4-diketogulonic acid, 3,4-diketogulonic acid, 1-keto-2,3,4-trihydroxyadipic acid, and 1,3,4-trihydroxy-2-ketoadipic acid, said in vivo concentrations being determined by the method of claim 8.

19. A method for detecting oxidative stress in a patient comprising determining the redox potential of a body fluid of said patient according to the method of claim 18.

* * * * *

UNITED STATES PATENT AND TRADEMARK OFFICE
CERTIFICATE OF CORRECTION

PATENT NO. : 5,212,096

DATED : May 18, 1993

INVENTOR(S) : J. Fred Kolhouse; John C. Deutsch

It is certified that error appears in the above-indentified patent and that said Letters Patent is hereby corrected as shown below:

On the cover page, Item [57], fourth line of text, please rewrite "potentials," as --potential-- and "fluid" as --fluids--. At column 2, line 27, please rewrite "13996" as --18996--. At column 7, line 38, please insert --A-- between "row" and "above". At column 7, lines 43-44, please rewrite "Chiral centers are marked with a double cross." as --Chiral centers in compounds A I-IV and B I-II are those carbons to which -OH is bound.-- At column 9, line 16, please rewrite "While" as --while--. At column 14, line 29,, please rewrite "Ouantitation" as --Quantitation--. At column 15, line 47, please rewrite "and" as --add--. At column 18, line 4 of claim 14, please delete the "." after "spectrometry" and insert --quantitation.-- thereafter.

Signed and Sealed this

First Day of February, 1994

Attest:

BRUCE LEHMAN

Attesting Officer

Commissioner of Patents and Trademarks